(12) United States Patent
Birrell et al.

(10) Patent No.: US 7,955,219 B2
(45) Date of Patent: Jun. 7, 2011

(54) EXERCISE COMMUNITY SYSTEM

(75) Inventors: James S. Birrell, Seattle, WA (US); Brady A. Olason, Mukilteo, WA (US); David W. Flynt, Lake Forest Park, WA (US); Autumn L. Stroupe, Kirkland, WA (US); David E. Dyer, Renton, WA (US)

(73) Assignee: Precor Incorporated, Woodinville, WA (US)

( * ) Notice: Subject to any disclaimer, the term of this patent is extended or adjusted under 35 U.S.C. 154(b) by 0 days.

(21) Appl. No.: 12/572,444

(22) Filed: Oct. 2, 2009

(65) Prior Publication Data

US 2011/0082007 A1 Apr. 7, 2011

(51) Int. Cl.
*A63B 71/00* (2006.01)
*A63B 23/00* (2006.01)

(52) U.S. Cl. ............................ 482/8; 482/9; 482/148

(58) Field of Classification Search ............. 482/8, 1–7, 482/9, 148, 900–902; 434/247
See application file for complete search history.

(56) References Cited

U.S. PATENT DOCUMENTS

| | | | |
|---|---|---|---|
| 4,720,789 A | 1/1988 | Hector et al. | 463/33 |
| 4,828,257 A | 5/1989 | Dyer et al. | 482/5 |
| 4,840,372 A | 6/1989 | Oglesby et al. | 482/9 |
| 4,955,602 A | 9/1990 | Rastelli | 482/84 |
| 4,998,725 A | 3/1991 | Watterson et al. | 482/6 |
| 5,062,626 A | 11/1991 | Dalebout et al. | 482/1 |
| 5,062,632 A | 11/1991 | Dalebout et al. | 482/7 |
| 5,067,710 A | 11/1991 | Watterson et al. | 482/3 |
| 5,104,120 A | 4/1992 | Watterson et al. | 482/5 |
| 5,149,084 A | 9/1992 | Dalebout et al. | 482/3 |
| 5,213,555 A | 5/1993 | Hood et al. | 482/57 |
| 5,383,826 A | 1/1995 | Michael | 482/3 |
| 5,466,200 A | 11/1995 | Ulrich et al. | 482/4 |
| 5,484,355 A | 1/1996 | King, II et al. | 482/4 |
| 5,489,249 A | 2/1996 | Brewer et al. | 482/5 |
| 5,512,025 A | 4/1996 | Dalebout et al. | 482/6 |
| 5,554,033 A | 9/1996 | Bizzi et al. | 434/247 |
| 5,591,104 A | 1/1997 | Andrus et al. | 482/7 |
| 5,645,509 A | 7/1997 | Brewer et al. | 482/4 |
| 5,655,997 A | 8/1997 | Greenberg et al. | 482/5 |
| 5,706,822 A | 1/1998 | Khavari | 600/483 |
| 5,777,895 A | 7/1998 | Kuroda et al. | 702/188 |
| 5,785,632 A | 7/1998 | Greenberg et al. | 482/5 |
| 5,888,172 A | 3/1999 | Andrus et al. | 482/7 |
| 5,890,995 A | 4/1999 | Bobick et al. | 482/4 |
| 5,916,063 A | 6/1999 | Alessandri | 482/4 |
| 5,931,763 A | 8/1999 | Alessandri | 482/4 |
| 6,042,519 A | 3/2000 | Shea | 482/57 |
| 6,053,844 A | 4/2000 | Clem | 482/8 |
| 6,059,692 A | 5/2000 | Hickman | 482/8 |
| 6,066,075 A | 5/2000 | Poulton | 482/8 |
| 6,152,856 A | 11/2000 | Studor et al. | 482/8 |
| 6,159,131 A | 12/2000 | Pfeffer | 482/8 |
| 6,171,218 B1 | 1/2001 | Shea | 482/57 |
| 6,193,631 B1 | 2/2001 | Hickman | 482/8 |
| 6,227,968 B1 | 5/2001 | Suzuki et al. | 463/7 |
| 6,244,988 B1 | 6/2001 | Delman | 482/8 |
| 6,312,363 B1 | 11/2001 | Watterson et al. | 482/54 |
| 6,330,499 B1 | 12/2001 | Chou et al. | 701/33 |
| 6,336,891 B1 | 1/2002 | Fedrigon et al. | 482/8 |

(Continued)

*Primary Examiner* — Rinaldi I Rada
*Assistant Examiner* — Robert F Long
(74) *Attorney, Agent, or Firm* — Terence P. O'Brien; Todd A. Rathe

(57) ABSTRACT

An exercise system provides incentives for individuals by providing either a collective exercise goal or a sponsored exercise reward.

20 Claims, 4 Drawing Sheets

U.S. PATENT DOCUMENTS

| | | | |
|---|---|---|---|
| 6,421,571 B1 | 7/2002 | Spriggs et al. | 700/17 |
| 6,447,424 B1 | 9/2002 | Ashby et al. | 482/8 |
| 6,458,060 B1 | 10/2002 | Watterson et al. | 482/54 |
| 6,464,618 B1 | 10/2002 | Shea | 482/8 |
| 6,475,115 B1 | 11/2002 | Candito et al. | 482/4 |
| 6,514,199 B1 | 2/2003 | Alessandri | 600/300 |
| 6,554,706 B2 | 4/2003 | Kim et al. | 463/36 |
| 6,572,512 B2 | 6/2003 | Anderson et al. | 482/51 |
| 6,601,016 B1 | 7/2003 | Brown et al. | 702/182 |
| 6,616,578 B2 | 9/2003 | Alessandri | 482/8 |
| 6,626,799 B2 | 9/2003 | Watterson et al. | 482/4 |
| 6,626,800 B1 | 9/2003 | Casler | 482/8 |
| 6,634,992 B1 | 10/2003 | Ogawa | 482/8 |
| 6,638,198 B1 | 10/2003 | Shea | 482/8 |
| 6,659,916 B1 | 12/2003 | Shea | 482/57 |
| 6,702,719 B1 | 3/2004 | Brown et al. | 482/8 |
| 6,746,371 B1 | 6/2004 | Brown et al. | 482/8 |
| 6,827,669 B2 | 12/2004 | Cohen et al. | 482/8 |
| 6,863,641 B1 | 3/2005 | Brown et al. | 482/8 |
| 6,866,613 B1 * | 3/2005 | Brown et al. | 482/8 |
| 6,902,513 B1 | 6/2005 | McClure | 482/8 |
| 6,918,858 B2 | 7/2005 | Watterson et al. | 482/54 |
| 6,921,351 B1 | 7/2005 | Hickman et al. | 482/8 |
| 6,971,973 B2 | 12/2005 | Cohen et al. | 482/8 |
| 6,991,586 B2 | 1/2006 | Lapcevic | 482/8 |
| 6,997,852 B2 | 2/2006 | Watterson et al. | 482/1 |
| 7,022,047 B2 | 4/2006 | Cohen et al. | 482/8 |
| 7,056,265 B1 | 6/2006 | Shea | 482/8 |
| 7,060,006 B1 | 6/2006 | Watterson et al. | 482/54 |
| 7,060,008 B2 | 6/2006 | Watterson et al. | 482/54 |
| 7,070,539 B2 | 7/2006 | Brown et al. | 482/8 |
| 7,121,982 B2 | 10/2006 | Feldman | 482/8 |
| 7,128,693 B2 | 10/2006 | Brown et al. | 482/8 |
| 7,166,062 B1 | 1/2007 | Watterson et al. | 482/8 |
| 7,166,064 B2 | 1/2007 | Watterson et al. | 482/4 |
| 7,217,224 B2 | 5/2007 | Thomas | 482/8 |
| 7,331,226 B2 | 2/2008 | Feldman et al. | 73/379.01 |
| 7,455,622 B2 | 11/2008 | Watterson et al. | 482/8 |
| 7,465,257 B1 * | 12/2008 | Morgan, Jr. | 482/57 |
| 7,491,153 B2 | 2/2009 | Li et al. | 482/8 |
| 7,507,183 B2 | 3/2009 | Anderson et al. | 482/1 |
| 7,521,623 B2 | 4/2009 | Bowen | 84/612 |
| 7,537,546 B2 | 5/2009 | Watterson et al. | 482/8 |
| 7,549,947 B2 | 6/2009 | Hickman et al. | 482/8 |
| 7,556,590 B2 | 7/2009 | Watterson et al. | 482/8 |
| 7,575,536 B1 | 8/2009 | Hickman | 482/8 |
| 7,594,873 B2 | 9/2009 | Terao et al. | 482/1 |
| 7,618,346 B2 | 11/2009 | Crawford et al. | 482/8 |
| 7,621,846 B2 | 11/2009 | Ainsworth et al. | 482/8 |
| 7,821,404 B2 * | 10/2010 | Walker et al. | 340/573.1 |
| 2002/0019258 A1 | 2/2002 | Kim et al. | 463/36 |
| 2002/0022551 A1 | 2/2002 | Watterson et al. | 482/8 |
| 2002/0055383 A1 | 5/2002 | Onda et al. | 463/36 |
| 2002/0055419 A1 | 5/2002 | Hinnebusch | 482/8 |
| 2002/0097150 A1 | 7/2002 | Sandelman et al. | 340/506 |
| 2002/0160883 A1 * | 10/2002 | Dugan | 482/8 |
| 2005/0102172 A1 * | 5/2005 | Sirmans, Jr. | 705/4 |
| 2007/0135264 A1 * | 6/2007 | Rosenberg | 482/8 |
| 2007/0219059 A1 * | 9/2007 | Schwartz et al. | 482/8 |
| 2007/0225118 A1 | 9/2007 | Giorno | 482/1 |
| 2007/0260482 A1 | 11/2007 | Nurmela et al. | 705/2 |
| 2007/0265138 A1 | 11/2007 | Ashby | 482/8 |
| 2007/0265139 A1 | 11/2007 | Glick | 482/8 |
| 2008/0051256 A1 | 2/2008 | Ashby et al. | 482/5 |
| 2008/0153670 A1 | 6/2008 | McKirdy et al. | 482/1 |
| 2008/0161654 A1 | 7/2008 | Teller et al. | 600/300 |
| 2008/0182723 A1 | 7/2008 | Aaron et al. | 482/8 |
| 2008/0200312 A1 * | 8/2008 | Tagliabue | 482/9 |
| 2008/0207401 A1 | 8/2008 | Harding et al. | 482/4 |
| 2008/0220941 A1 | 9/2008 | Shaw et al. | 482/9 |
| 2009/0023553 A1 | 1/2009 | Shim | 482/4 |
| 2009/0075781 A1 | 3/2009 | Schwarzberg et al. | 482/8 |
| 2009/0098980 A1 | 4/2009 | Waters | 482/8 |
| 2009/0098981 A1 | 4/2009 | Del Giorno | 482/9 |
| 2009/3011165 | 4/2009 | Sullivan et al. | 482/4 |
| 2009/0118100 A1 | 5/2009 | Oliver et al. | 482/8 |
| 2009/0139389 A1 | 6/2009 | Bowen | 84/636 |
| 2009/0144080 A1 | 6/2009 | Gray et al. | 705/2 |
| 2009/0149299 A1 * | 6/2009 | Tchao et al. | 482/9 |
| 2009/0156364 A1 | 6/2009 | Simeoni | 482/9 |
| 2009/0163321 A1 | 6/2009 | Watterson et al. | 482/4 |
| 2009/0219159 A1 | 9/2009 | Morgenstern | 340/573.1 |
| 2009/0221404 A1 | 9/2009 | Dorogusker et al. | 482/8 |
| 2009/0233770 A1 | 9/2009 | Vincent et al. | 482/8 |
| 2009/0233771 A1 * | 9/2009 | Quatrochi et al. | 482/9 |
| 2009/0239709 A1 | 9/2009 | Wu | 482/8 |
| 2009/0240113 A1 | 9/2009 | Heckerman | 600/300 |
| 2009/0253554 A1 | 10/2009 | McIntosh | 482/4 |
| 2009/0258758 A1 | 10/2009 | Hickman et al. | 482/8 |
| 2009/0262088 A1 | 10/2009 | Moll-Carrillo et al. | 345/173 |
| 2009/0269728 A1 * | 10/2009 | Verstegen et al. | 434/247 |
| 2009/0270227 A1 | 10/2009 | Ashby et al. | 482/8 |
| 2009/0298650 A1 * | 12/2009 | Kutliroff | 482/8 |

* cited by examiner

EXERCISE COMMUNITY SYSTEM

CROSS-REFERENCE TO RELATED PATENT APPLICATIONS

The present application is related to co-pending application Ser. No. 12/572,448 filed on the same date herewith by David E. Dyer, James S. Birrell, Brady A. Olason, Brian D. Wilson, David W. Flynt, and Autumn L. Stroupe and entitled EXERCISE GUIDANCE SYSTEM, the full disclosure of which is hereby incorporated by reference.

BACKGROUND

Exercising is largely an individualistic activity. Due to the lack of community, a person exercising may lack sufficient encouragement or motivation to maintain a disciplined exercise regimen or to achieve his or her health objectives.

DETAILED DESCRIPTION OF THE EXAMPLE EMBODIMENTS

Figure 1:
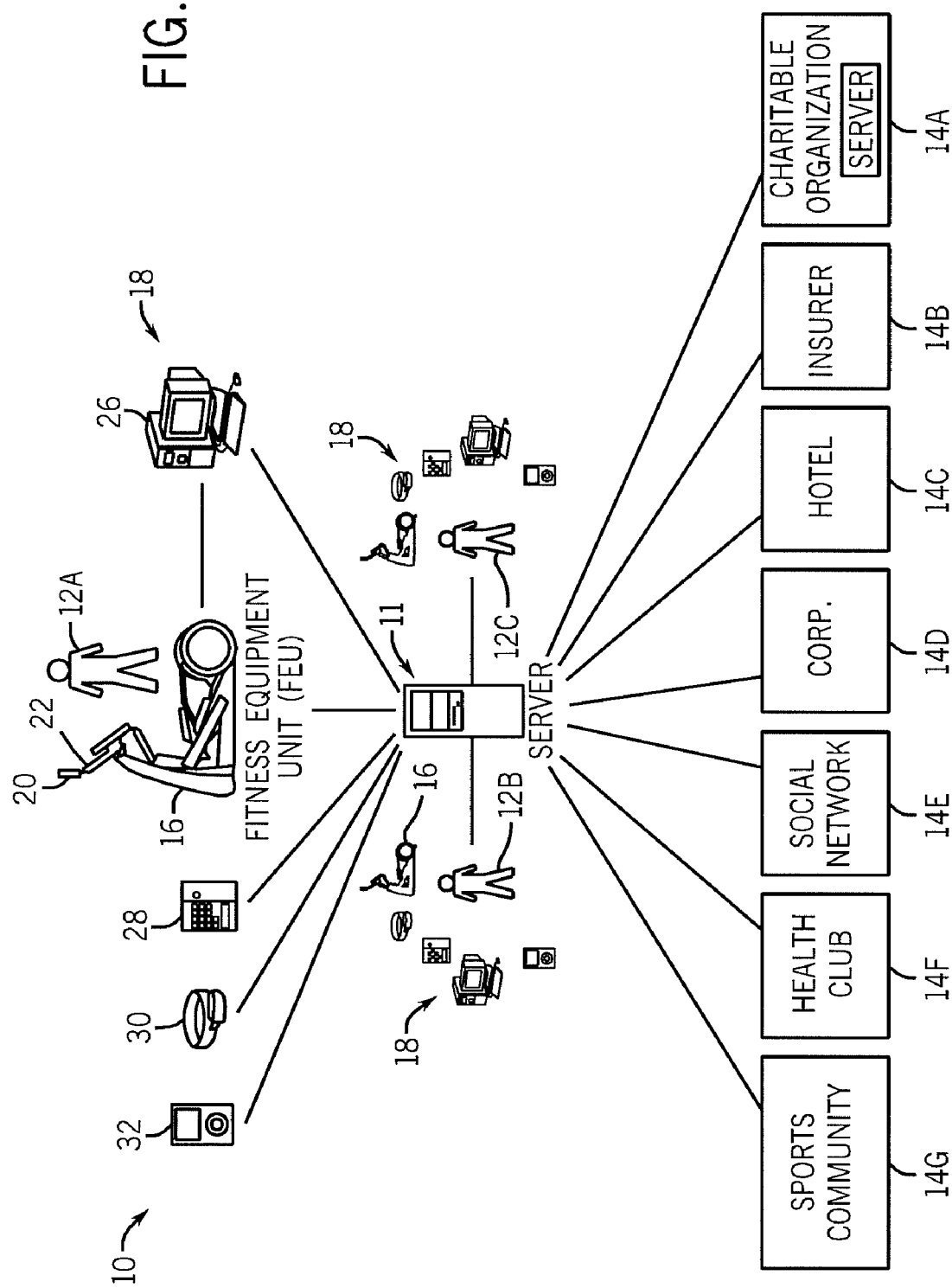
FIG. 1 is a schematic illustration of an exercise community system according to an example embodiment.

FIG. 1 schematically illustrates an exercise community system 10 according to an example embodiment. Exercise community system 10 comprises a communications hub 11 of one of more servers interconnecting multiple individuals 12A, 12B and 12C (collectively referred to as individuals 12) to one another and to one or more third-party content and motivational sources or providers 14A-14G (collectively referred to as source providers 14). As will be described hereafter, exercise community system 10 provides a sense of community to persons who are exercising and provides a source of motivation to assist in the maintenance of a disciplined exercise regimen. In particular, system 10 delivers three motivational aspects: sharing, belonging and competition.

As shown by FIG. 1, each individual 12 has an associated exercise device or fitness equipment unit (FEU) 16 and one or more communication peripherals 18. In the example illustrated, FEU 16 is illustrated as an elliptical exercise device. In other embodiments, FEU 16 may comprise other exercise devices such as a treadmill, a stair-stepper, or other high or low impact cardio trainers or strength training equipment. FEU 16 is configured to receive force or motion from a person exercising. FEU 16 is further configured to provide a controlled and potentially adjustable resistance to the motion or force received from a person exercising such that the intensity of a workout may be adapted to the needs of the individual.

FEU 16 additionally includes a display 20 and an input 22 by which individual 12 may interact with FEU 16. In particular, display 20 provides individual 12 with feedback as well as exercising suggestions. In one embodiment, display 20 comprises a display screen. In another embodiment, display 20 comprises one or more light emitting diodes. In still other embodiments, display 20 may provide auditory feedback. In particular embodiments, display 20 may include more than one display component types.

Input 22 facilitates the input of commands, data or requests to FEU 16. Input 22 may comprise a touchpad, a touch screen (potentially incorporated as part of display 20), a keyboard, push buttons, toggle switches, slider bars and the like. In some embodiments, input 22 may comprise a microphone and associated speech recognition software. Input 22 permits an individual identify himself or herself, to provide input regarding his or her health or fitness attributes, to select or adjust exercise routines and to communicate with other individuals 12 or third party organizational entities.

Although FEU 16 is illustrated as being associated with individual 12, FEU 16 need not necessarily be owned by individual 12. For purposes of this disclosure, with respect to FEU's 16, the term "associated" means that any moment in time, a particular individual 12 is exercising using FEU 16 and is providing or receiving information via hub 11. An individual may associate himself or herself with an FEU 16 by signing in or logging into system 10 and hub 11 while on a particular exercise device or FEU 16. In some circumstances, FEU 16 may be located in a gym, hotel, or health or fitness club. In other circumstances, FEU 16 may be located in a person's office, home or other personal non-public location. Regardless of where situated, once connected to hub 11, FEU 16 is configured to communicate with other FEU's 16, with communication peripherals 18 of other individuals as well as with motivational providers 14 via hub 11.

Communication peripherals 18 comprise devices configured to receive and potentially transmit data using hub 11. Peripherals 18 may have a variety of sizes, shapes and configurations. FIG. 1 illustrates various example communication peripherals that may be used by an individual 12 when not exercising. Such examples include, but are not limited to, laptop or desktop computers 26, cell phones 28, personal training devices wearables 30 (such as wrist mounted personal trainers, wrist mounted computers or wrist mounted watches) and personal data assistants (PDA's) 32. Communication devices may include displays by which exercise data or exercise routines may be presented to an individual 12 when not exercising for evaluation, selection or adjustment.

Hub 11 interconnects each of multiple individuals 12 with one another and with other third parties, such as motivational sources 14. In one embodiment, hub 11 comprises one or more servers configured to communicate via a local network or a larger network such as the internet. In one embodiment, hub 11 comprises a server of a manufacturer of a plurality of exercise devices or FEUs 16. Hub 11 operates according to one or more sets of instructions contained in software code, integrated circuits or other computer-readable programs or medium stored in some form persistent memory or embodied as a circuit. Hub 11 allows an individual 12 to communicate with other individuals 12 and with third parties when exercising on FEU 16 or while using one of his or her communication peripherals 18. FEU 16 or communication peripherals 18 not only communicate with hub 11 but may also upload information to or download information from hub 11. Examples of data or information that may be communicated include, but is not limited to, workout information, media, advertisements and the like. As a result, hub 11 provides a person exercising with a greater sense of community.

Figure 2:
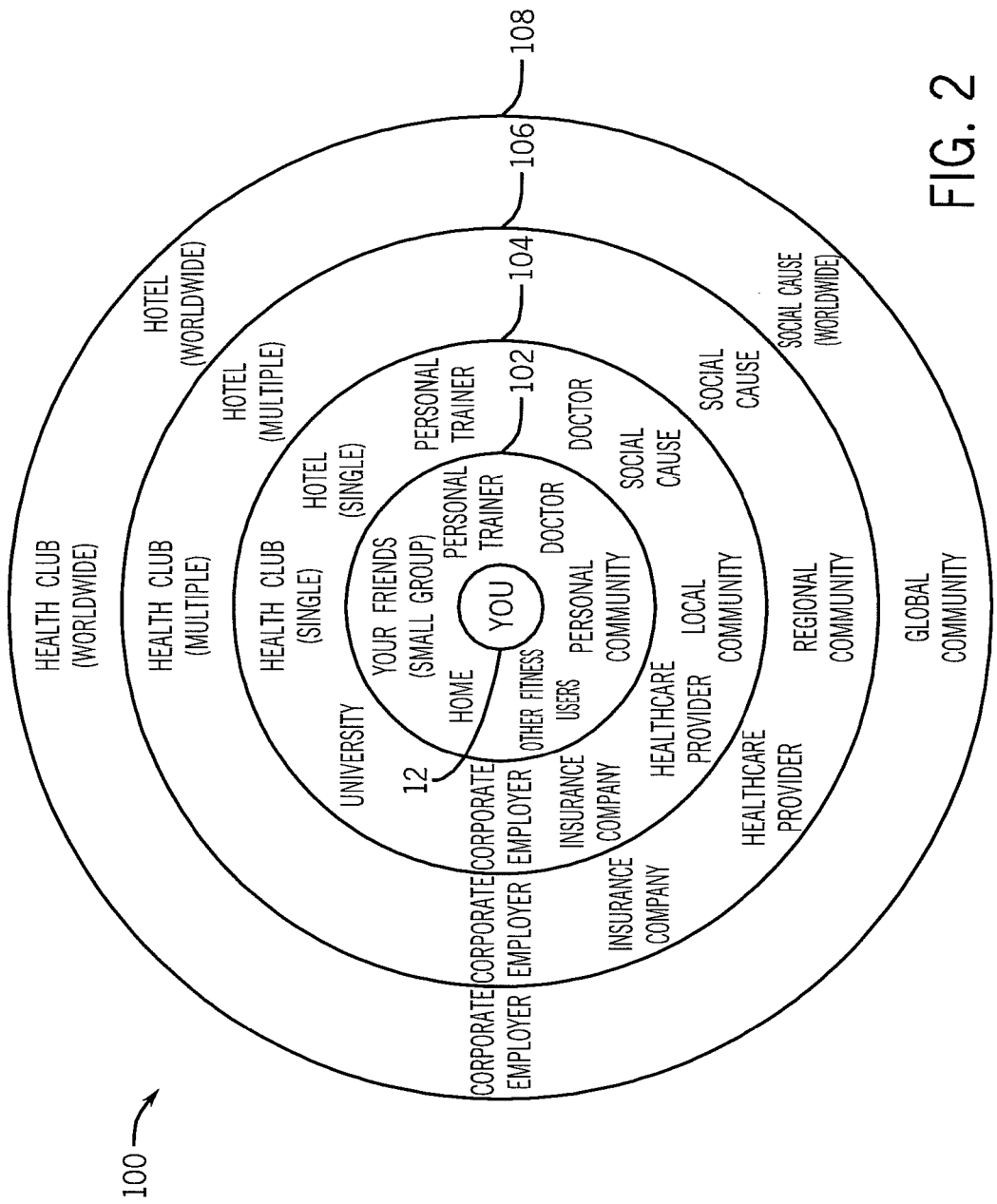
FIG. 2 is a schematic diagram of a community that may be established as part of a profile used in the system of FIG. 1.

FIG. 2 is a schematic diagram illustrating one example set of "circles" or "rings" constituting an example community 100 to which an individual 12 may belong. In the example illustrated, community 100 includes four levels or rings of relationships: a personal community ring 102, a local community ring 104, a regional community ring 106 and a global community ring 108. In the example illustrated, the personal community ring 102 includes friends of the individual 12, his or her home or family, his or her personal trainer, personal doctor and civic other fitness users which may have the same interests or associations.

The local community ring 104 includes such entities as social causes, doctors, personal trainers, single hotels, single health clubs, universities, corporate employers, insurance companies and healthcare providers. The regional community ring 106 may include a social cause, multiple hotels or groups of hotels, multiple health clubs or groups of health clubs, a corporate employer, an insurance company, and a healthcare provider. The global community ring 108 may also include social causes, worldwide hotels, worldwide health clubs and corporate employers. What particular entities are located within each of rings 102-104 is determined by the individual 12. It should be understood that the illustrated community 100 is one example of such a community. A particular individual's community may have a greater or fewer number of circles or levels and the number of entities within each community may be varied.

In the example illustrated, hub 11 is configured to prompt the individual 12 to create or establish a personal profile. In particular, the individual 12 is prompted to input (using an input 22 of FEU 16 or any input of peripherals 18) those entities that the person desires to be within each of the aforementioned rings. Each level or ring may be assigned with different levels of security and access to information from the individual 12. For example, those entities located in the innermost or intimate personal community ring 102 may have access to a first degree or amount of personal information of individual 12. Those entities located in or assigned to more outer rings may have access to more defined areas of information. In one embodiment, a profile may be created by hub 11 which provides a doctor or personal trainer with up-to-date exercise parameters or fitness indicators as sensed by FEU 16 during exercise such as weight, heart rate, exercise routine, exercise frequency, time and dates of exercise and even fitness or exercise goals or objectives. The same profile for individual 12 may provide access to a lesser extent of information to those individuals located in more outer rings. As a result, individuals can choose to extend their reach and visibility to the community 100 to ever larger circles or rings as they deem relevant.

In one embodiment, hub 11 may further be configured to utilize the created profile to automatically download or access information from different entities located in different levels or rings. For example, in one embodiment, the profile may be created such that hub 11 automatically downloads information from a personal trainer or doctor assigned to personal community ring 102. At the same time, the profile may require hub 11 to request confirmation before downloading data or information from those entities in more outer rings. With such a profile, individual 12 may define the inflow and outflow of information to reduce information overload or clutter and to identify and gather information most relevant or important to the individual 12. In a similar fashion, other individuals 12 may establish profiles including the individual 12 in their inner rings of community 100.

In one embodiment, hub 11 may be configured to automatically notify other individuals 12 that the individual 12 is exercising at any moment in time. For example, profile may be set up such that selected friends are automatically notified when an individual 12 begins exercising on any FEU 16 connected to hub 11. Such notifications may be reciprocal. As a result, while the individual 12 is exercising, he or she may be informed of other individuals 12 in his or her community 100 who are also exercising at the same time. As a result, the individual 12 may not feel as alone when he or she is exercising. Consequently, system 10 provides those individuals 12 or exercising with a sense of sharing and belonging.

In particular embodiments, hub 11 may additionally provide other individuals 12 in selected rings of a person's community 100 with access to or additional information regarding the exercise being performed by the individual 12 or metrics of each other's workout. For example, a group of individuals 12 may be simultaneously alerted as to each other's levels of performance, workout intensity, type of workout and goals. In effect, hub 11 simulates an environment where multiple individuals 12 who are friends or associates effectively workout or exercise together as exercise or workout "partners." Such workout partners may see each other's progress so that they may provide or offer encouragement and accountability to one another. As exercise partners, individuals may also share content and media between one another as well as messages. For example, one individual may recommend an exercise or course to another individual 12.

In some circumstances, hub 11 may facilitate competitions between such workout partners. Examples of competitions that may be facilitated by hub 11 include, but not limited to, challenges regarding fitness goals, exercise intensity, weight loss, workout frequency and the like. In some embodiments, hub 11 may facilitate the establishment of shared exercise or fitness goals amongst multiple individuals 12.

In the example illustrated, hub 11 is further configured to store exercise or workout results from individual 12. Hub 11 may further be configured to provide the stored exercise results to other individuals 12 within designated community rings (as established by the profile) at other times when a particular individual 12 is not exercising. As a result, the benefits of sharing and community between different individuals 12 during exercise may be achieved even when the individuals do not exercise at the same time. Because the exercise results are stored by hub 11, such competitions may be based upon long-term exercise objectives or results extended over multiple workout sessions.

For example, in one embodiment, hub 11 is configured to store and collect a collective exercise goal of a plurality of individuals who exercise. Hub 11 communicates with each of FEU 16 used at different times by the individuals 12 and receives exercise results from FEU 16. Hub 11 further compares the received exercise results to the collective exercise goal. After the exercise results of different individuals 12 are combined or otherwise aggregated, and compared to the collective excise goal, the comparison results are provided to each of the individual exercisers via display 20 or displays associated with peripherals 18. Such comparison results may be transmitted via e-mails or may be made available on a website that is available to each of the individuals 12.

In addition to facilitating sharing, belonging and competition amongst individuals 12 who share the common interest or objective of fitness, hub 11 further facilitates the sharing of such information with third party entities 14. As shown in FIG. 1, examples of third-party entities include, but are not limited to, charitable organizations 14A, insurers 14B, hotels 14C, corporations 14D, social networks 14E, health clubs 14F and sports communities 14G. Each of such third-party entities may provide an individual 12 who is exercising with additional sources of motivation facilitated by hub 11 of system 10.

Figure 3:
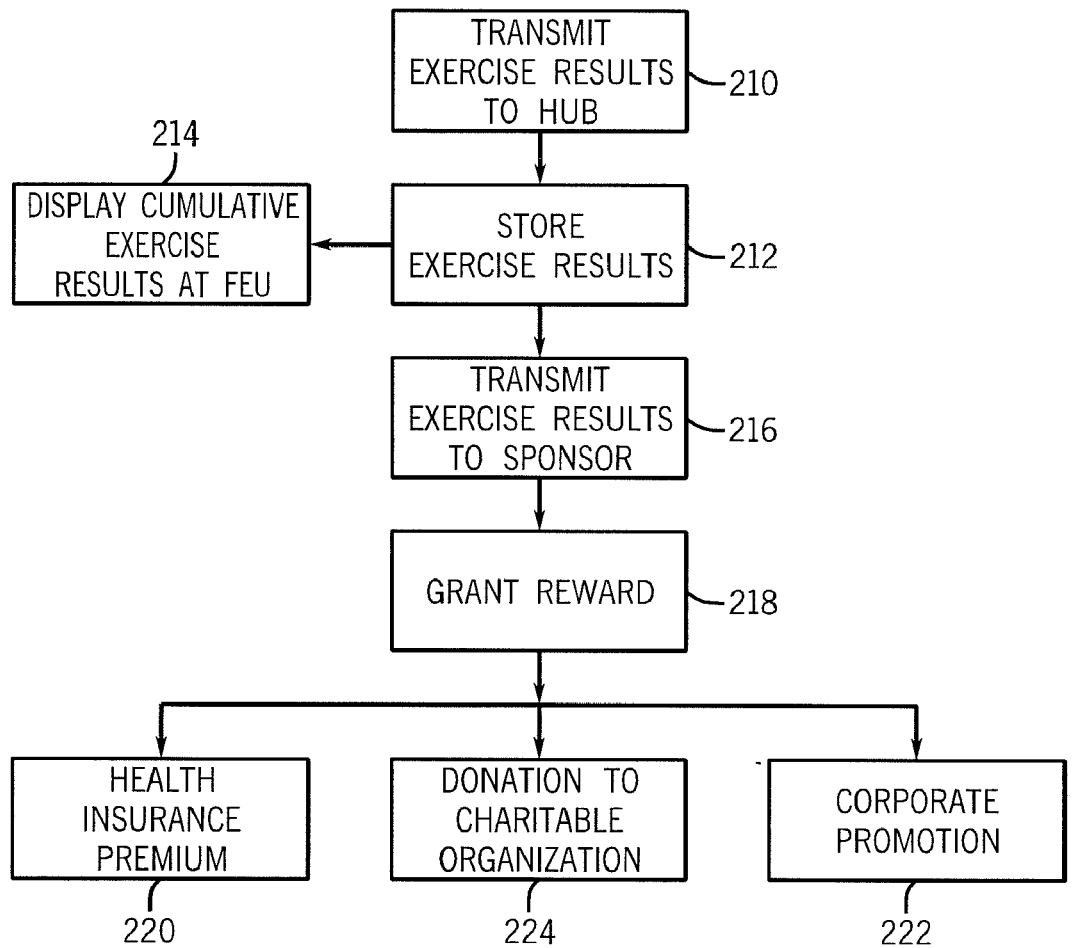
FIG. 3 is a flow diagram of a method that may be carried out by the system of FIG. 1 for providing exercise motivation.

FIG. 3 is a flow diagram illustrating one method 200 by which additional motivation may be provided to those individuals 12 exercising or who are partaking in an exercise regime facilitated by hub 11. As shown by step 210, upon completion of an exercise workout by an individual 12, his or her exercise results are transmitted by FEU 16 to hub 11. The transmittal of the exercise results may be done in a wired fashion or wirelessly via an internet connection or other communication mode. In some embodiments, the collection of exercise results by the web server of hub 11 may be automatic and may be initiated upon the beginning of a workout. In other embodiments, the individual 12 may connect to hub 11 and transmit the exercise results to hub 11. In some embodiments, the collection of exercise results may be automatic or may merely require a confirmation depending upon the profile of the individual.

As indicated by step 212, hub 11 stores the exercises results in a persistent storage device or memory. As indicated by step 214, the received exercise results as well as the accumulated exercise results may additionally be displayed to the individual at display 20 of FEU 16 while the person is exercising on FEU 16 or after the individual has just completed exercising on FEU 16. Alternatively, the exercise results may be displayed on one or more of peripherals 18 connected to hub 11. Examples of exercise results that may be received, stored and displayed include, but are not limited to, distances covered during one or more workouts, heart rates achieved during the one or more workouts, workout intensity, workout duration, workout frequency and the like.

As indicated by step 216, hub 11 further transmits the exercise results to one or more exercise sponsors such as one of more third-party entities 14 shown in FIG. 1. As indicated by step 218, upon a predefined fitness, exercise or workout objective or goal being satisfied, the one or more sponsors may grant a reward to or on behalf of the individual 12 who has satisfied the goal. For example, as indicated by step 220, in one embodiment, the reward granted in step 218 may comprise a health insurance premium adjustment or reduction. Health insurance companies or healthcare providers 14B may desire to offer incentives for those insured that exercise or maintain a certain fitness level. System 10 and hub 11 facilitate the collection of exercise results or exercise data by the health insurance providers or healthcare providers, allowing confirmation of such fitness objective being met. At the same time, the health insurance provider 14B may communicate back to the person or individual 12 exercising during this exercise so as to encourage individual while he or she is exercising. In one embodiment, the exercise results may be directly communicated to the health insurance provider. In another embodiment, the health insurance provider may provide hub 11 with fitness objectives or standards that must be met before a reward may be authorized, wherein hub 11 simply notifies a health insurance provider when the objective has been met and authorizes granting of the reward.

As indicated by step 222, in one embodiment, the reward granted may be a corporate promotion. Certain companies or corporations may desire to reward those who maintain a certain level of fitness. Some companies that manufacture, sell or service fitness equipment, health drinks, health food and the like may desire to reward those individuals 12 who exercise or who use their products. System 10 and hub 11 facilitate the collection of exercise results or exercise data by the health insurance providers or healthcare providers, allowing confirmation of such fitness objective being met. At the same time, the corporate sponsor 14D may communicate to the person or individual 12 who is exercising so as to encourage the individual while he or she is exercising. In one embodiment, the excise results may be directly communicated to the corporate sponsor. In another embodiment, the corporate sponsor provider may provide hub 11 with fitness objectives or standards that must be met before a reward may be authorized, wherein hub 11 simply notifies the corporate sponsor when the objective has been met and authorizes granting of the reward.

As indicated by step 222, in one embodiment, the reward granted may be a donation to a charitable organization on behalf of the individual 12. In a fashion similar to a walkathon or other charitable event, individuals may collect donations to a charitable cause or charitable organization based upon certain fitness objectives or workout goals being met or based in a pro rata manner upon some exercise metric. For example, donations to a charitable organization may be made based upon the number of miles or number of hours that a person exercises on a treadmill, elliptical machine or the like. System 10 and hub 11 facilitate the collection of exercise results or exercise data by the charitable organization running the charitable event or the donors themselves, allowing confirmation of such fitness objective being met or the metric results of exercise. At the same time, the charitable donors may receive notification of when the individual 12 if working out or exercising for the charitable cause on their peripheral devices 18. As a result, the charitable donors may communicate to the person or individual 12 who is exercising so as to encourage the individual while he or she is exercising. In one embodiment, the exercise results may be directly communicated to the charitable organization 14A (to one or more servers of the charitable organization 14B. As a result, system 10 and hub 11 provide exercise motivation to an individual 12 while also promoting various charitable causes.

In other embodiments, hub 11 of system 10 may motivate individual 12 exercising by offering rewards from other sponsors such as hotels 14C, social networks 14E, the health clubs themselves 14F or sports communities 14G. Such sponsors may offer rewards directly to the individual exercising or may offer donations or contributions on behalf of the individual 12 exercising. Examples of social networks include, but are not limited to, FACEBOOK and TWITTER. Examples of sports communities include support organizations such as US Track and Field (USTAF), NIKEPLUS and others.

Figure 4:
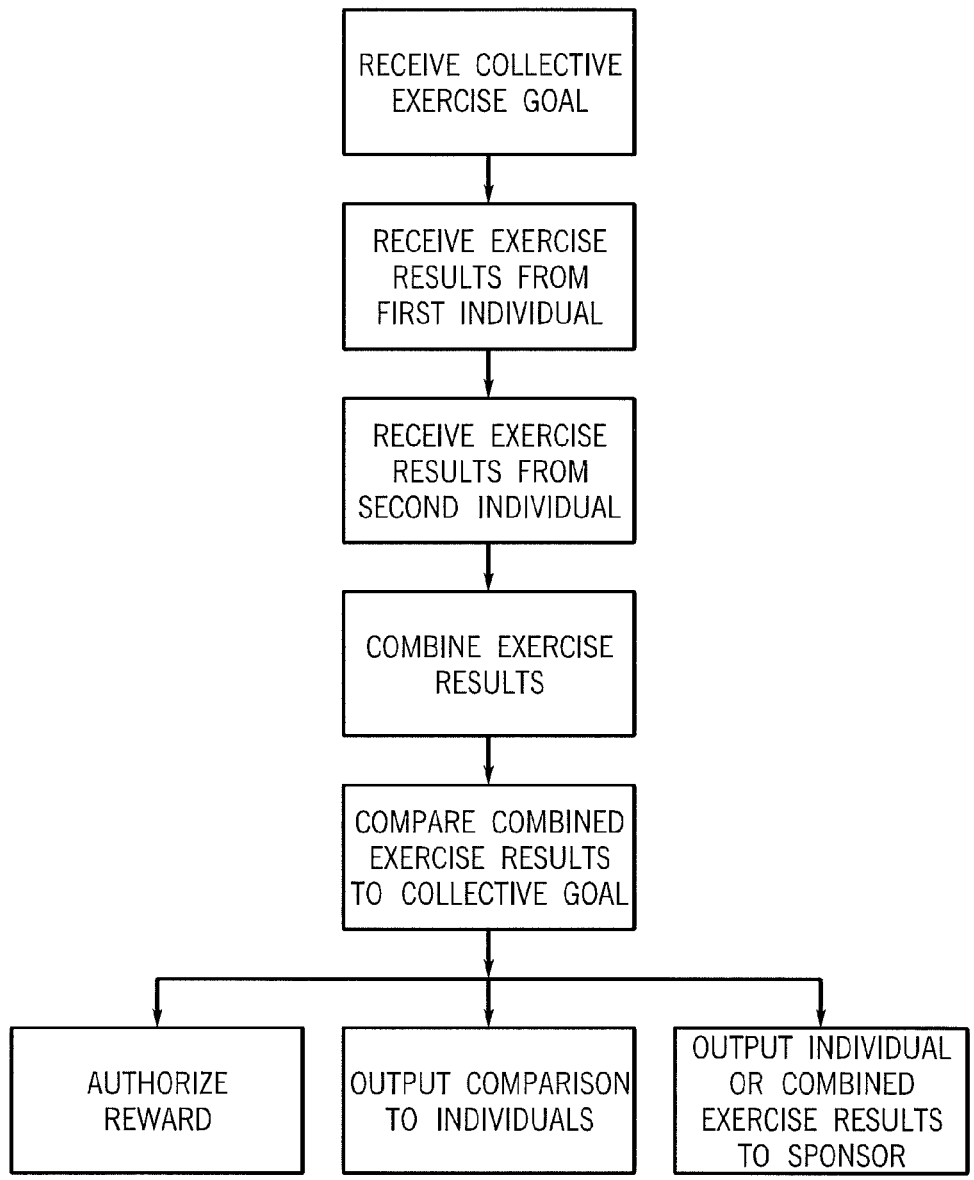
FIG. 4 is a flow diagram of another method that may be carried out by the system of FIG. 1 for providing exercise motivation.

In addition to providing rewards and exercise motivation on individual basis, system 10 and hub 11 further provide boards and exercise motivation on a group level, once again facilitating a sense of sharing and belonging to those individuals exercising. FIG. 4 is a flow diagram of a method 300 for providing motivational assistance at a group level. As indicated by step 310, hub 11 initially receives or collects exercise goal from two or more individuals 12 via either input 22 or inputs associated with peripherals 18. This collective exercise goal is stored and associate with each of the individuals 12. Examples of such a collective exercise goal include a sum of exercise results from multiple individuals 12 or an average, median or other statistic derived from the exercise results of multiple individuals 12 or exercising. In one embodiment, the collective exercise goal is based upon excise metrics from a same type of FEU 16 in communication with hub 11. In another embodiment, the collective exercise goal may be associated with multiple different types of FEUs 16. For example, the click of exercise goal may involve exercise on both treadmills and elliptical machines. In one embodiment, hub 11 adjusts or modifies exercise results or handicaps certain excise results to establish a uniform standard amongst different types of exercise devices or FEUs.

As indicated by steps 312 and 314, hub 11 receives (or collects) exercise results from each of the individuals 12 while they are exercising, upon completion of their workout or upon the uploading of exercise results from each of individuals 12 from intermediate peripherals 18 which have temporally stored the exercise results. As indicated by step 316, hub 11 combines or otherwise aggregates the exercise results of the multiple individuals 12. In one embodiment, hub 11 adjusts or modifies exercise results or handicaps certain exercise results to establish a uniform standard amongst different types of exercise devices or FEUs.

As indicated by step 318, hub 11 compares the collective exercise goal (received or established in step 310) to the combined or otherwise aggregated exercise results from multiple individuals 12. This comparison yields a comparison result. As indicated by step 320, the results of this comparison are output to one or more the individuals 12. As a result, they want a more individuals 12 may see how they contribute towards the overall collective goal and how individuals 12, as a group, or moving towards the collective goal. In one embodiment, the comparison results may be presented numerically or graphically, such as with a bar graph, pie chart and the like graphically illustrating the collective goal being met. In one embodiment, the comparison result may be outputted tricky to the exercise machines or FEUs 16 as movement towards the collective goal is achieved, providing the person exercising with motivation during exercise.

As indicated by steps 322 and 324, the collective goals established in step 310 may also be awarded in a manner similar to the individual motivating towards described above. For example, a third-party entity such as a charitable organization, an insurance company, corporate sponsor and the like may establish a collective goal (in place of the goal input in step 310) for a group of multiple individuals 12. Upon the collective goal being met, each of the individuals 12 may receive an individual reward (such as a health care insurance premium reduction, frequent flyer miles or other product bonus or cost reduction). In other embodiments, the group of individuals 12 may receive a donation or cost reduction for their particular organization or group. Still another embodiment, a charitable donation a made on behalf of the group of individuals to a charitable cause our charitable organization. The reward may be authorized by hub 11 as indicated in step 324 or the individual or aggregated exercise results may be directly forwarded by hub 11 to one or more third-party reward sponsors.

Overall, system 10 and hub 11 provide a network by which individuals 12 who exercise may communicate with other individuals who exercise and may also communicate with third-party entities interested in promoting such exercise. System 10 and hub 11 facilitate a sense of sharing, belonging and competition. System 10 and hub 11 promote more disciplined workout regimens and benefit worthy charitable causes.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. An exercise system comprising:
a plurality of exercise devices, wherein the exercise devices are configured to sense and transmit exercise results;
at least one server storing a collective exercise goal of a plurality of individuals, the least one server in communication with a plurality of exercise devices so as to receive the exercise results and to compare the exercise results to the collective exercise goal, wherein the least one server provides comparison results to the individuals, wherein the at least one server is of a manufacturer of the plurality of exercise devices and wherein the system further comprises at least one second server of an exercise reward sponsor, wherein the least one second server receives the exercise results from the at least one first server.

2. The exercise system of claim 1, wherein the at least one server authorizes a reward in response to the collective exercise goal being met.

3. The exercise system of claim 2, wherein the plurality of exercise devices each includes a display and wherein the at least one server or the at least one second server is configured to transmit current and total accumulated levels of current donations to the display of at least one of the plurality of exercise devices.

4. The exercise system of claim 2, wherein the reward comprises a donation to a charitable organization.

5. The exercise system of claim 3, wherein the donation is pro-rata based upon a value of the exercise result.

6. The exercise system of claim 1, wherein the reward comprises a health insurance premium reduction for one or more of the individuals.

7. The exercise system of claim 1, wherein the plurality of exercise devices includes at least one elliptical exercise device.

8. The exercise system of claim 1, wherein the collective exercise goal comprises an average of the exercise results from the individuals.

9. The exercise system of claim 1, wherein the collective exercise goal comprises a sum or average of the exercise results from the individuals on different types of exercise devices.

10. The exercise system of claim 1, wherein the at least one server receives and stores exercise results from a plurality of distinct exercise sessions of one of the individuals.

11. An exercise incentive system comprising:
an exercise device configured to transmit first exercise results of a first individual to at least one web server;
wherein the at least one web server receives the first exercise results and transmits the first exercise results or information based upon the first exercise results to an exercise incentive sponsor that provides a reward based upon the exercise results and wherein the at least one server is configured to store a profile for the first person identifying a second person and wherein the at least one server is configured to automatically notify the first person on one of the plurality of exercise devices when the second person is concurrently exercising on another of the plurality of exercise devices.

12. The exercise incentive system of claim 11, wherein the reward comprises a donation to a charitable organization on behalf of the individual.

13. The exercise incentive system of claim 11, wherein the at least one web server transmits the reward authorization to the exercise incentive sponsor.

14. The exercise incentive system of claim 11, wherein the exercise incentive sponsor comprises an insurance company.

15. The exercise incentive system of claim 14, wherein the reward comprises a health insurance premium reduction or credit.

16. The exercise incentive system of claim 11 further comprising a second exercise device configured to transmit second exercise results of a second individual to the at least one server, wherein the at least one server receives the second exercise results of the second individual, combines the first exercise results and the second exercise results, and transmits the combined exercise results to the first individual or the second individual.

17. The exercise incentive system of claim 16, wherein the at least one server transmits the combined exercise results to the exercise incentive sponsor.

18. An exercise system comprising:
a plurality of exercise devices, wherein the exercise devices are configured to sense and transmit exercise results;
at least one server storing a collective exercise goal of a plurality of individuals, the least one server in communication with a plurality of exercise devices so as to receive the exercise results and to compare the exercise results to the collective exercise goal, wherein the least one server provides comparison results to the individuals;
at least one input and display associated with one of the plurality of exercise devices or a peripheral;
at least one computing device configured to cause the display to prompt a person to input groupings of entities by the input, wherein the groupings are assigned different levels of access to exercise information from an exercise device being used by the person.

19. An exercise system comprising:
a plurality of exercise devices, wherein the exercise devices are configured to sense and transmit exercise results;
at least one server storing a collective exercise goal of a plurality of individuals, the least one server in communication with a plurality of exercise devices so as to receive the exercise results and to compare the exercise results to the collective exercise goal, wherein the least one server provides comparison results to the individuals at least one input and display associated with one of the plurality of exercise devices or a peripheral;
at least one computing device configured to cause the display to prompt a person to input groupings of entities by the input, wherein the groupings are assigned different levels of information inflow authorization requirements.

20. An exercise system comprising:
a plurality of exercise devices, wherein the exercise devices are configured to sense and transmit exercise results;
at least one server storing a collective exercise goal of a plurality of individuals, the least one server in communication with a plurality of exercise devices so as to receive the exercise results and to compare the exercise results to the collective exercise goal, wherein the least one server provides comparison results to the individuals, wherein the collective exercise goal comprises a sum or average of the exercise results from the individuals on different types of exercise devices and wherein the at least one server is configured to store a profile for the first person identifying a second person and wherein the at least one server is configured to automatically notify the first person on one of the plurality of exercise devices when the second person is concurrently exercising on another of the plurality of exercise devices.

* * * * *